(12) United States Patent
Burren et al.

(10) Patent No.: US 11,541,189 B2
(45) Date of Patent: Jan. 3, 2023

(54) INJECTION DEVICE WITH A CAP FOR REMOVING A NEEDLE PROTECTION CAP FROM A PRODUCT CONTAINER, AND METHOD FOR PROVIDING SUCH AN INJECTION DEVICE

(71) Applicant: Ypsomed AG, Burgdorf (CH)

(72) Inventors: Stefan Burren, Schwarzenburg (CH); Jürg Hirschel, Bern (CH); Markus Tschirren, Burgdorf (CH); Andres Mellenberger, Koppigen (CH)

(73) Assignee: Ypsomed AG, Burgdorf (CH)

( * ) Notice: Subject to any disclaimer, the term of this patent is extended or adjusted under 35 U.S.C. 154(b) by 412 days.

(21) Appl. No.: 16/906,556

(22) Filed: Jun. 19, 2020

(65) Prior Publication Data
US 2020/0330699 A1 Oct. 22, 2020

Related U.S. Application Data

(63) Continuation of application No. PCT/IB2018/059650, filed on Dec. 5, 2018.

(30) Foreign Application Priority Data

Dec. 21, 2017 (CH) ..................................... 01586/17

(51) Int. Cl.
  *A61M 5/32* (2006.01)
  *A61M 5/20* (2006.01)
(52) U.S. Cl.
  CPC ........ *A61M 5/3204* (2013.01); *A61M 5/2033* (2013.01)
(58) Field of Classification Search
  CPC . A61M 5/3204; A61M 5/2033; A61M 5/3202
  (Continued)

(56) References Cited

U.S. PATENT DOCUMENTS 9,339,610 B2 5/2016 Julian et al.
2016/0220764 A1* 8/2016 Durvasula ......... A61M 5/31596
(Continued)

FOREIGN PATENT DOCUMENTS

CH 714489 A2 6/2019
EP 2255842 B1 5/2017
(Continued)

OTHER PUBLICATIONS

International Search Report and Written Opinion received for International Application No. PCT/IB2018/059650, dated Mar. 25, 2019, 15 pages.

(Continued)

*Primary Examiner* — Bhisma Mehta
*Assistant Examiner* — Nidah Hussain
(74) *Attorney, Agent, or Firm* — Dorsey & Whitney LLP

(57) ABSTRACT

This relates to an injection device comprising a housing for receiving a product container, which has a rigidly connected injection needle, and a cap for removing a needle protection cap from the product container. The cap comprises an engagement element in order to carry out the removal of the needle protection cap from the product container while removing the cap from the injection device. The cap further comprises a rotating sleeve, wherein the rotating sleeve has a reverse rotation protection element, and the engagement element or the housing has a reverse rotation protection counter-element in order to allow a rotation of the rotating sleeve in one direction and block the rotation in the opposite direction.

15 Claims, 4 Drawing Sheets

(58) Field of Classification Search
USPC .......................................................... 604/192
See application file for complete search history.

(56) References Cited

U.S. PATENT DOCUMENTS

2016/0243315 A1    8/2016  Perche et al.
2017/0354790 A1*  12/2017  Atterbury ........... A61M 5/2033
2019/0001065 A1*   1/2019  Daniel ................ A61M 5/2033

FOREIGN PATENT DOCUMENTS

WO    2010136076 A1    12/2010
WO    2013085454 A1     6/2013
WO    2015144871 A1    10/2015
WO    2016205963 A1    12/2016
WO    2019123073 A1     6/2019

OTHER PUBLICATIONS

International Preliminary Report on Patentability received for International Application No. PCT/IB2018/059650, dated Jun. 23, 2020, 9 page.

* cited by examiner

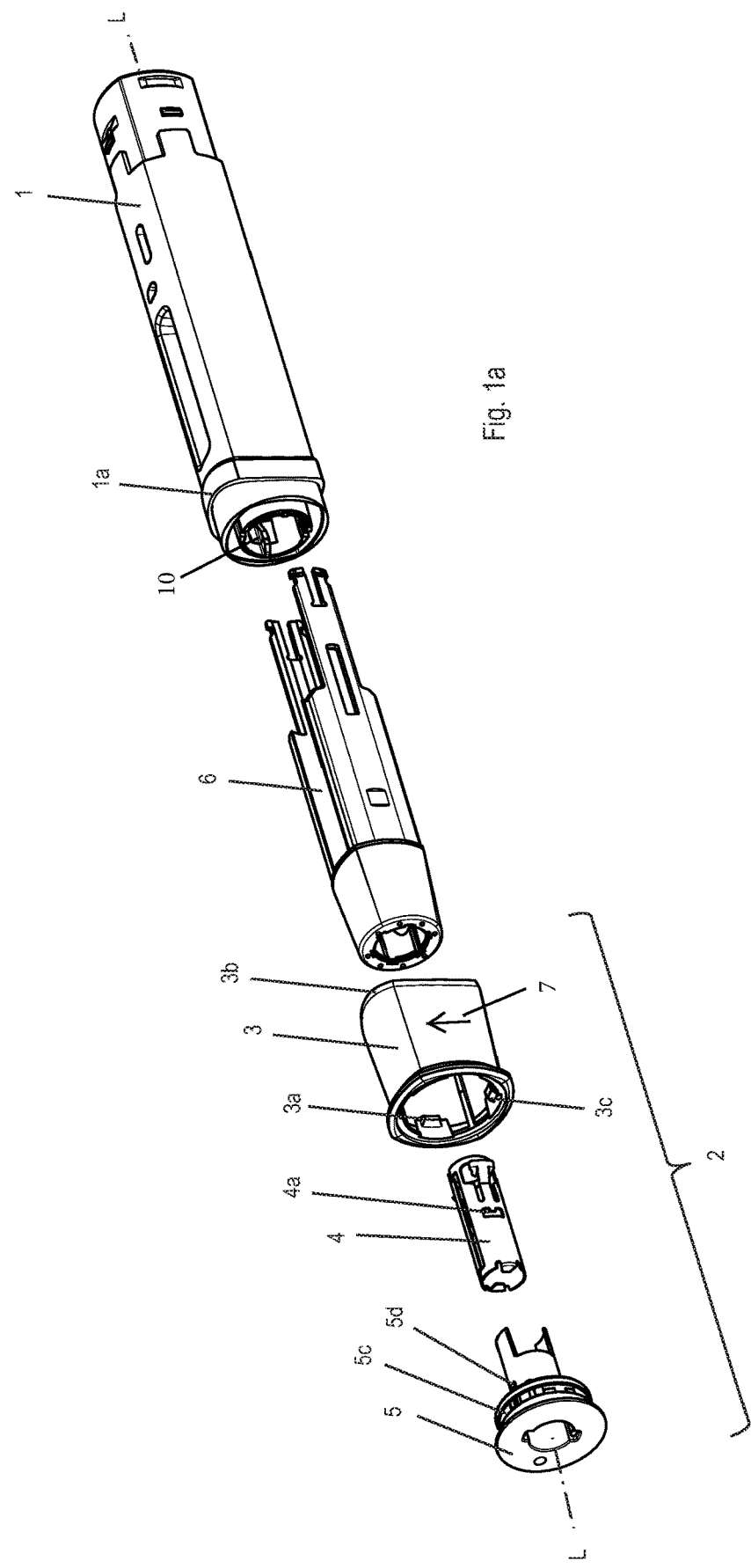

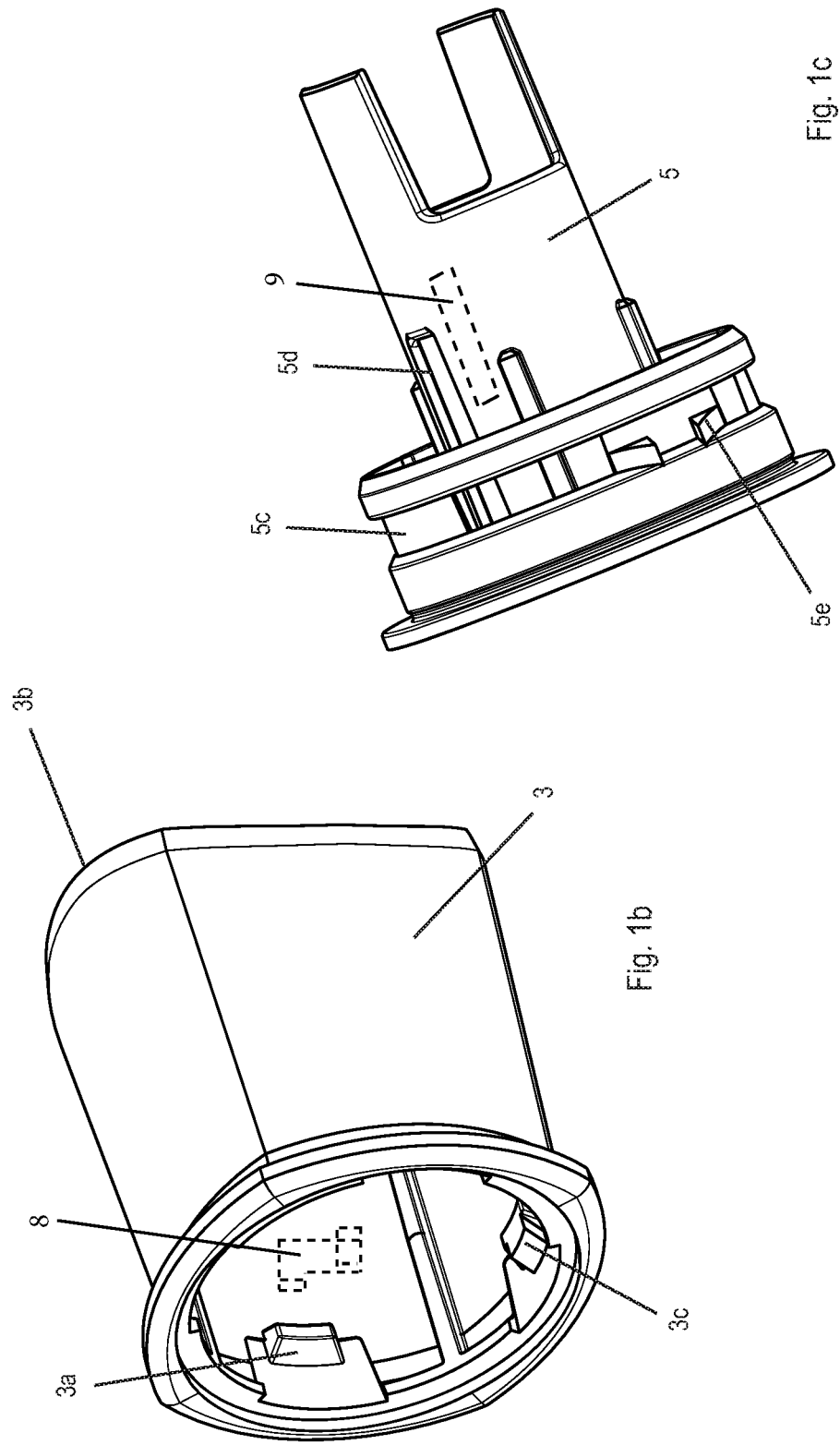

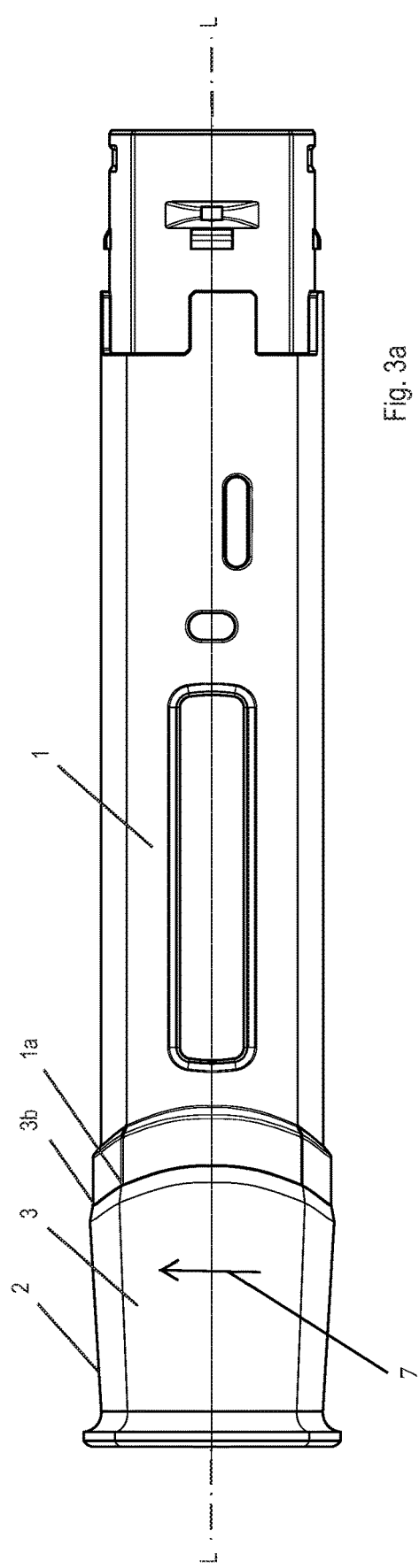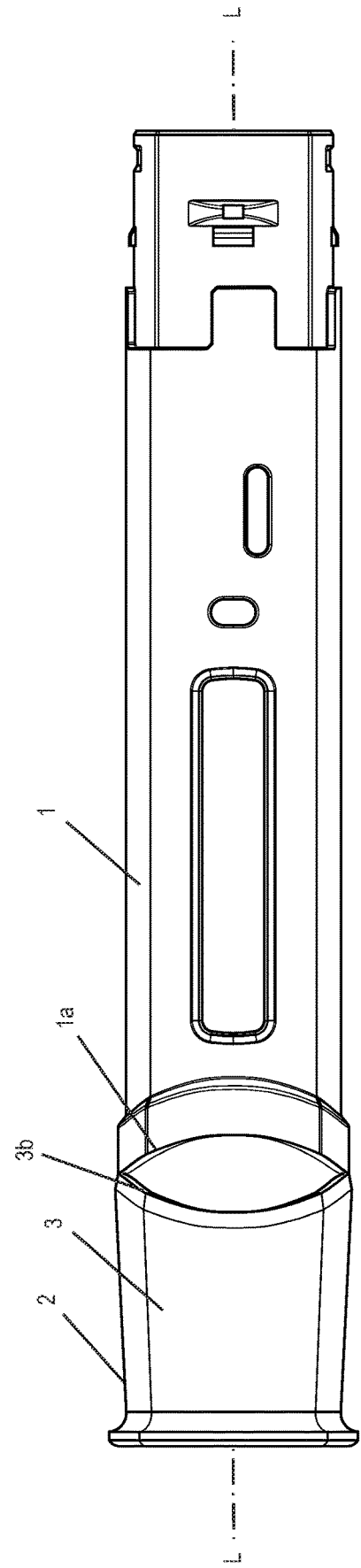

INJECTION DEVICE WITH A CAP FOR REMOVING A NEEDLE PROTECTION CAP FROM A PRODUCT CONTAINER, AND METHOD FOR PROVIDING SUCH AN INJECTION DEVICE

This application claims priority to International Application No. PCT/IB2018/059650, filed Dec. 5, 2018, entitled "INJECTION DEVICE WITH A CAP FOR REMOVING A NEEDLE PROTECTION CAP FROM A PRODUCT CONTAINER, AND METHOD FOR PROVIDING SUCH AN INJECTION DEVICE", which in turn claims priority to Swiss Application No. 01586/17 filed Dec. 21, 2017 entitled "INJECTION DEVICE WITH A CAP FOR REMOVING A NEEDLE PROTECTION CAP FROM A PRODUCT CONTAINER, AND METHOD FOR PROVIDING SUCH AN INJECTION DEVICE", each of which is incorporated by reference herein, in the entirety and for all purposes.

The invention relates to an injection device for administering a liquid product, in particular a drug. The invention further relates to a method for preparing such an injection device for the administration of a product.

Here, the term "drug" comprises any flowable medical formulation which is suitable for controlled administration through a means such as a cannula or a hollow needle, comprising, for example, a liquid, a solution, a gel or a fine suspension containing one or more medical substances. "Drug" can refer to a composition with a single active substance or to a premixed or a co-formulated composition with a plurality of active substances from a single container. Drug comprises medicines such as peptides (for example, insulins, insulin-containing drugs, GLP-1-containing preparations as well as derived or analogous preparations), proteins and hormones, biologically prepared or active substances, active substances based on hormones or genes, nutrition formulations, enzymes and other substances either in solid (suspended) or liquid form but also polysaccharides, vaccines, DNA or RNA, or oligonucleotides, antibodies or parts of antibodies as well as suitable base substances, adjuvants and carrier substances.

From the prior art, injection devices are known in which a pre-filled syringe is arranged. The pre-filled syringe comprises an injection needle which is non-detachably connected to the pre-filled syringe and through which a drug contained in the pre-filled syringe can be dispensed. In order to keep the injection needle and the drug of the pre-filled syringe sterile, the injection needle is enclosed in a needle protection cap fastened to the pre-filled syringe and sealed in a sterile manner with respect to the environment. Such needle protection caps can be designed, for example, as a so-called soft needle shield (SNS) or as a rigid needle shield (RNS). A soft needle shield (SNS) consists of an elastomer portion which surrounds the injection needle. A rigid needle shield (RNS) comprises multiple parts, in particular an elastomer cap-shaped portion and a sleeve-shaped portion produced from a solid or rigid, i.e., a non-elastomer, plastic which receives the elastomer portion and is thus connected substantially non-detachably.

In order to be able to inject a drug contained in the pre-filled syringe, the needle protection cap has to be removed from the pre-filled syringe. From WO 2010/136076 A1, U.S. Pat. No. 9,339,610 B2, WO 2015/144871 A1 and US 2016/0243315 A1, it is known that, when pulling off a cap-shaped pull-off element, also referred to as cap, which is attached on the distal end of the injection device and which closes the distal end of the injection device, the needle protection cap attached on the pre-filled syringe is also pulled off, i.e., it is removed from the pre-filled syringe during the removal of the cap. The needle protection cap here remains in the cap. For this purpose, the cap comprises engagement members which are brought in engagement with the needle protection cap during the pulling off of the cap. During the continuation of the pull-off movement of the pull-off element, the engagement members entrain the needle protection cap, whereby said needle protection cap is pulled off the pre-filled syringe. In order to ensure a reliable pulling off of the needle protection cap by the removal of the cap, it is known from the prior art that the engagement members connected to the cap are in engagement with the needle protection cap. Furthermore, from EP 2255842 B1, it is known that by rotation of the cap the needle protection cap can be pulled off the pre-filled syringe. Here, during the pulling off of the needle protection cap, the pull off force is dependent on the path of the rotation of the cap, wherein the pull-off force during the rotation of the cap is smaller than the pull-off force during an axial movement of the cap.

One aim of the invention is to provide an injection device and a method for the preparation of such an injection device for the administration of a product, which enables a more reliable and/or simpler removal of the needle protection cap from the product container.

The aim is achieved by the injection device according to claims below and by the method according to other claims below. Advantageous developments appear in the dependent claims, the description and the figures.

The disclosed apparatus starts with a device for the administration of a product, namely an injection device having a longitudinal axis (L). The injection device can be designed as a so-called autoinjector, which comprises a mechanism for carrying out an automatic dispensing of the product, such as, for example, by means of an energy storage system, in particular a spring, and optionally for carrying out automated insertion and/or retraction of the injection needle. In an autoinjector, the force for dispensing the product is provided by the energy storage system such as, for example, the spring. The injection device can alternatively also be designed as a manual injection device, i.e., such that the force for dispensing the product is generated by muscle force exerted, for example, by the users themselves. The injection device—regardless of whether it is an autoinjector or a manual injection device—can comprise a needle protection sleeve which, after the injection has occurred, protrudes distally over the distal end of the injection needle or is shifted relative to the housing into this position, in order to prevent accidental access to the injection needle and thereby reduce the risk of injury. In an autoinjector, the needle protection sleeve can also be used, for example, as a triggering element for triggering the product dispensing, wherein the needle protection sleeve is shifted for this purpose relative to the housing in the proximal direction. Alternatively, the triggering of the autoinjector can be achieved by actuating a triggering button of the autoinjector, wherein the needle protection sleeve is used as shield before the use of the autoinjector.

The injection device comprises a product container with an injection needle such as, for example, a pre-filled syringe known from the prior art or in general a syringe. The product container may comprise, for example, a hollow cylindrical product container section which serves to mount a piston in a manner so that it can be shifted. The piston may form a seal with the inner periphery of the product container section and in this way form a sterile barrier. The piston may be shifted, for example, by means of a piston rod of the injection device, in the distal direction in order to dispense product via the injection needle from the product container. The injection needle may be formed preferably nondetachably on the product container. For example, the product container may comprise a holding section, in particular a needle holding section, which is arranged distally of the product container section and nondetachably connected to the injection needle and thus, for example, surrounds a proximal portion of the injection needle. The injection needle may thus protrude from the holding section in the distal direction. The holding section may have, for example, a smaller outer diameter than the product container section. The product container section may taper at its distal end toward the holding section.

The term "distal" used herein refers to the direction in which the tip of the injection needle points. The term "proximal" used herein refers to the direction opposite the distal direction.

On the product container, for example, on the holding section, a needle protection cap such as, for example, a soft needle shield (SNS) or a rigid need shield (RNS) known from the prior art is fastened, in particular detachably fastened. The needle protection cap can be fastened, for example, by a friction or positive-locking connection or by a combination of friction and positive-locking connections on the holding section. The needle protection cap encloses the injection needle and seals it in a sterile manner with respect to the environment. A soft needle shield (SNS) comprises or consists of an elastomer, for example, a portion formed from a rubber or caoutchouc based material, which surrounds the needle. The soft needle shield (SNS) on its outer periphery has a soft surface formed, for example, from a rubber or caoutchouc based material. A rigid needle shield (RNS) usually comprises multiple portions, in particular an elastomer cap-shaped inner portion and a sleeve-shaped or cap-shaped outer portion produced from a stiffer, i.e., non-elastomer, plastic, which receives the elastomer portion and is thus substantially nondetachably connected. The outer sleeve- or cap-shaped portion surrounds the inner cap-shaped portion and, for example, is nondetachably connected to the inner cap, so that the outer and inner caps form one unit. The outer portion can be formed from a harder plastic than the inner portion. For example, the outer portion can be made of polyethylene, polystyrene, polypropylene or another suitable plastic. The inner portion can be formed, for example, from rubber or caoutchouc or another suitable material.

On the distal end of the injection device or of a housing such as, for example, a receiving housing of the injection device, a cap, which may also be referred to or designed as a closure cap or pull-off cap, may be fastened and close the distal end of the housing or of the receiving housing. The injection device may comprise a housing such as, for example, a receiving housing of the injection device for receiving the product container, wherein the product container comprises a rigidly connected injection needle and wherein the needle protection cap is detachably arranged on the product container. The needle protection cap encloses the injection needle and seals the injection needle in a sterile manner with respect to the environment. The cap may be connected, for example, to the housing or receiving housing by friction and/or positive-locking connection, such as, for example, by snap connection. The cap may be removable, for example, during the removal from the injection device or the housing, by means of a combined axial rotation movement and an axial movement of the injection device, such as, for example, the housing or receiving housing.

The injection device may moreover comprise a product container holder which is rigidly connected to the housing of the injection device, in particular in an axially and rotationally fixed manner. The product container holder may be used for receiving the product container, wherein, in the product container holder, the product container may be held rigidly, in particular in an axially and preferably rotationally fixed manner. Alternatively, the housing and the product container may be designed to form a single part. Alternatively, the product container holder may be arranged in such a manner that it can be axially moved relative to the housing and/or rotated.

The cap which is detachably provided on the distal end of the housing of the injection device comprises one or more engagement elements in order to carry out the removal of the needle protection cap from the product container during the removal of the cap from the injection device. The cap which is coupled to the engagement element may be connectable to the needle protection cap via the engagement element(s) in such a manner that the removal of the cap from the injection device carries out the removal of the needle protection cap from the product container. In particular, at least some of the movement or the entire movement of the cap in the distal direction may be transmitted to the engagement element, i.e., so that the engagement element is entrained by the cap in such a way that the engagement element pulls the needle protection cap from the product container, in particular from the holding section. Preferably, the engagement element is arranged in a rotationally fixed manner relative to the housing.

In an embodiment, the engagement element may be deformable in such a manner that the engagement element may be brought from a spaced position in which the engagement element is radially spaced from the needle protection cap into an engagement position in which the engagement element is in engagement with the needle protection cap, wherein the engagement element is deformed during the removal of the cap. In the delivery state of the injection device, the engagement element may be, for example, in the spaced position with respect to the needle protection cap. In the engagement position, the engagement element is arranged with respect to the needle protection cap in such a manner that a movement of the cap in the distal direction entrains the needle protection cap and thus the needle protection cap is removed from the product container. In the engagement position of the engagement element, the engagement element engages on or in the needle protection cap. The engagement element may engage on or in a lateral surface or on or in an edge or on or in a distal front surface or on or in a proximal front surface of the needle protection cap. The engagement element may comprise a hook or multiple hooks. Particularly preferably, the engagement element may be formed at least partially in the shape of a hook. Particularly preferably, the engagement element may moreover be formed in the shape of a sleeve or in the shape of a cylinder. The hook-shaped engagement element may have a short and a long leg. Preferably, the long leg is designed to be deformable. Furthermore, the short leg may be designed to be in the shape of a tooth or a triangle or an acute angle. Alternatively, the engagement element may also have another design, wherein, in the spaced position of the engagement element, the engagement element is radially spaced from the needle protection cap, and, in the engagement position of the engagement element, the engagement element is engaged with the needle protection cap, wherein the engagement element is deformed during the removal of the cap.

In the spaced position of the engagement element, the engagement element may be undeformed, deformed or deformed radially outward. In the engagement position of the engagement element, the engagement element may be undeformed, deformed or deformed radially inward. The engagement element may preferably be plastically and/or resiliently deformable.

A permanent deformation is referred to as a plastic deformation. The deformation of a material is plastic when the material on its own does not again assume its original shape. After the action of a force or load on the material, the material maintains its shape. A reversible deformation is referred to as a resilient deformation. Here, after the action of a force or a load on a material, the material again assumes its original shape.

The engagement element is preferably formed from metal, in particular from steel, particularly preferably from stainless steel or spring steel. The engagement element is formed from a material which has a bending strength which allows a plastic and/or resilient deformation. Particularly preferably, the engagement element is designed in such a manner that, in the spaced position of the engagement element, it is plastically and/or resiliently deformed, and, in the engagement position, it is plastically and/or resiliently undeformed, or in that, in the spaced position of the engagement element, it is plastically and/or resiliently undeformed, and, in the engagement position it is designed to be plastically and/or resiliently deformed.

Furthermore, on the housing or on a portion rigidly connected on the housing, one or more blocking elements may be provided, wherein, in the engagement position, the blocking element(s) hold(s) or bring(s) the engagement element in engagement with the needle protection cap. The blocking element may comprise a first and/or a second inclined surface, in particular a first and/or a second inwardly protruding inclined surface. The first and/or the second inclined surface(s) of the blocking element may have an inclination. The first and the second inclined surfaces may be inclined toward one another. The engagement element of the cap is coupled in such a manner to the blocking element of the housing that, during the removal of the cap from the injection device, the engagement element may be or is moved relative to the needle protection cap and, during this movement, in particular during an axial movement, it may be or is deformed by means of the blocking element of the housing in such a manner that the engagement element, in particular the short leg of the engagement element, can come in engagement or be in engagement with the needle protection cap. In the engagement position of the engagement element, the engagement element is connected in an axially fixed manner to the needle protection cap, wherein the needle protection cap is entrained by the engagement element of the cap during the continuation of the combined axial rotation movement of the cap. In other words, the travel which the cap performs during the removal from the injection device relative to the housing along the longitudinal axis (L) in the distal direction comprises a first partial travel during which the cap may be or is moved relative to the needle protection cap, and a second partial travel during which the needle protection cap also performs the movement of the cap or is entrained by the cap.

In an alternative embodiment, one or more engagement elements may be provided, which are designed to be resiliently and/or plastically deformable, and wherein the one or more engagement elements are always and/or already in contact with the needle protection cap during the assembly of an injection device for the administration of a product. This assembly process furthermore comprises the shifting or introduction of a product container with the detachably connected needle protection cap in a housing along a longitudinal axis (L) in a distal direction, wherein the housing has a cap on a distal end. An outer lateral surface of the needle protection cap here slides axially over the engagement element(s), in particular on the short leg(s) of the engagement element. In the position in which the product container is introduced in the housing, the engagement element(s) of the cap is/are in an engagement position.

In an alternative embodiment, the cap may be moved with one or more engagement elements relative to a needle protection cap in the proximal direction, in order to put the cap on a product container received in the housing.

The lateral surface of the needle protection cap may have one or more openings or one or more fastening means, into which, in the engagement position of the engagement element, the engagement element may engage or project. Alternatively, the needle protection cap comprises no opening or no fastening means, wherein the engagement element in the engagement position of the engagement element can engage or project into the lateral surface of the needle protection cap.

Furthermore, the cap may comprise a rotating sleeve, wherein the rotating sleeve at least partially has received the engagement element, and it may rotate relative to the housing and relative to the engagement element about the longitudinal axis (L) and is arranged in an axially fixed manner relative to the engagement element. Preferably, the engagement element and the rotating sleeve are arranged concentrically with respect to one another. The rotating sleeve and the housing each comprise a wave-shaped or curve-shaped guiding slide link, which slide links are designed in such a manner or interact in such a manner that the rotating sleeve may rotate relative to the housing about the longitudinal axis (L), and the rotating sleeve and the engagement element can axially move relative to the housing in the distal direction. The engagement element is arranged in a rotationally fixed manner relative to the housing. The wave-shaped or curve-shaped guiding slide link is in sliding contact with the wave-shaped or curve-shaped guiding slide link of the housing. Particularly preferably, the distal end of the rotating sleeve comprises the wave-shaped or curve-shaped guiding slide link which is in sliding contact with the wave-shaped or curve-shaped guiding slide link of the housing, wherein the guiding slide link of the housing is formed as a projection or web which extends peripherally on or from an outer lateral surface of the housing. Particularly preferably, the wave-shaped or curve-shaped guiding slide links of the rotating sleeve and of the housing are designed in such a manner and interact in such a manner (e.g., akin to camming action) that, after a relative rotation of the rotating sleeve by approximately 90° about the longitudinal axis (L), the rotating sleeve is placed relative to the housing in a most distal position. This means that, during a relative rotation of the rotating sleeve by approximately 90° about the longitudinal axis (L), the rotating sleeve is moved relative to the housing by a maximum axial path in a distal direction. During the rotation of the rotating sleeve about the longitudinal axis (L), an axial movement of the engagement element in the distal direction occurs simultaneously, wherein the engagement element is in engagement or is brought into engagement with the needle protection cap.

The rotating sleeve may preferably be formed from plastic. Alternatively, the rotating sleeve may be formed from metal. The rotating sleeve may be connected, for example, to the housing of the injection device in a friction and/or positive-locking connection, such as, for example, by snap connection. For this purpose, for example on the rotating sleeve, an engagement member may be provided which can be detachably engaged in a counter-engagement member attached on the housing. The rotating sleeve may be removed with a combined axial rotation movement and an axial movement from the injection device, in particular from the housing. In particular, the rotating sleeve may be removed in a first step by a combined axial rotation movement and in a second step by axial removal from the injection device, in particular from the housing.

The rotating sleeve comprises a reverse rotation lock element, and the engagement element or the housing comprises a reverse rotation lock counter-element, in order to enable a rotation of the rotating sleeve about the longitudinal axis (L) in one direction and block it in the opposite direction. The reverse rotation mechanism of the injection device is used to ensure that the user can rotate the rotating sleeve only in one rotation direction relative to the engagement element or relative to the housing. A rotation of the rotating sleeve about the longitudinal axis (L) is possible in one direction and blocked in the opposite direction.

Particularly preferably, the reverse rotation lock element of the rotating sleeve and/or the reverse rotation lock counter-element of the engagement element or of the housing may comprise a toothing or latch or be formed as a toothing or a latch. For this purpose, the rotating sleeve may comprise one or more teeth which interact with one or more teeth of the engagement element or of the housing in such a manner that a rotation of the rotating sleeve about the longitudinal axis (L) is possible in one direction and blocked in the opposite direction. The corresponding toothing or latch comprises corresponding sliding surfaces and abutment surfaces, in order to enable a rotation of the rotating sleeve about the longitudinal axis (L) in one direction and block it in the opposite direction.

In an alternative embodiment, the reverse rotation lock element of the rotating sleeve and/or the reverse rotation lock counter-element of the engagement element or of the housing may comprise a spring arm or be formed as a spring arm. Furthermore, the reverse rotation lock element of the rotating sleeve and/or the reverse rotation lock counter-element of the engagement element or of the housing may comprise a projection, a web, a depression, a groove or a recess, by which rotation is possible about the longitudinal axis (L) in one direction and is blocked in the opposite direction.

Furthermore, the cap can comprise a sleeve-shaped or cylinder-shaped spacer sleeve which is connected in an axially fixed and rotationally fixed manner to the engagement element, and wherein the rotating sleeve is arranged in such a manner that it may rotate relative to the spacer sleeve. Alternatively, the spacer sleeve and the engagement element may be designed to form a single piece. Alternatively, the engagement element may comprise the spacer sleeve. Particularly preferably, the rotating sleeve and the spacer sleeve may be in a guiding engagement, in such a manner that the rotating sleeve is rotatable relative to the spacer sleeve about the longitudinal axis (L). Moreover, the spacer sleeve may be connected in a rotationally fixed manner to the housing. The spacer sleeve is preferably produced from plastic. Alternatively, the spacer sleeve may be manufactured from the same material as the engagement element.

In an alternative embodiment, it is possible that no spacer sleeve is provided. The rotating sleeve and the engagement element may be in a guiding engagement, in such a manner that the rotating sleeve may rotate relative to the engagement element about the longitudinal axis (L). Moreover, the engagement element may be connected in a rotationally fixed manner to the housing.

In an alternative embodiment, the rotating sleeve may rotate by a rotation angle about the longitudinal axis (L) in one direction, wherein, after the rotation of the rotating sleeve by a certain rotation angle, a rotation of the rotating sleeve about the longitudinal axis (L) in the opposite direction is blocked. For this purpose, the rotating sleeve may comprise a reverse rotation cam, and the spacer sleeve may comprise a reverse rotation projection, which interact in such a manner that, during the rotation of the rotating sleeve about the longitudinal axis (L) in one direction, the reverse rotation cam may slide over the reverse rotation projection, but, during the rotation of the rotating sleeve about the longitudinal axis (L) in the opposite direction, the reverse rotation cam comes in abutment contact with the reverse rotation projection, and the rotation in the opposite direction is blocked.

In an alternative embodiment, the rotating sleeve may rotate in a first and/or in a second rotation direction about the longitudinal axis (L), wherein, after the rotation of the rotating sleeve by a certain rotation angle about the longitudinal axis (L) in the first and/or the second rotation direction, a rotation of the rotating sleeve about the longitudinal axis (L) in the opposite direction of the first and/or the second rotation direction is blocked. For this purpose, the rotating sleeve may comprise a reverse rotation cam, and the spacer sleeve may comprise a pair of reverse rotation projections which interact in such a manner that, during the rotation of the rotating sleeve about the longitudinal axis (L) in a first and/or a second direction, the reverse rotation cam may slide over the reverse rotation projection, but, during the rotation of the rotating sleeve about the longitudinal axis (L) in the direction opposite the first and/or the second direction, the reverse rotation cam comes in abutment contact with one of the reverse rotation projections, and the rotation in the opposite direction is blocked.

Alternative designs of the reverse rotation lock element of the rotating sleeve and/or of the reverse rotation counter-element of the engagement element or of the housing may be provided, so that a rotation of the rotating sleeve about the longitudinal axis (L) is possible in one direction and blocked in the opposite direction.

Furthermore, the rotating sleeve, the engagement element and/or the housing may have a visual marking, particularly in the form of a symbol, particularly preferably in the form of an arrow, in order to indicate in which direction a rotation of the rotating sleeve about the longitudinal axis (L) is possible. This marking is used for a simpler operation of the injection device. In alternative embodiments, in addition or alternatively, an acoustic and/or tactile marking may be provided.

Furthermore, a needle protection sleeve may preferably be provided, wherein the cap is detachably connected via the needle protection sleeve to the housing. The needle protection sleeve is preferably arranged in a rotationally fixed manner relative to the housing. The needle protection sleeve is used so that before or after the injection has occurred, it distally protrudes over the distal end of the injection needle. The needle protection sleeve is partially received by the housing, wherein the cap can be put on a distal end of the needle protection sleeve. The cap may be connected, for example, to the needle protection sleeve, by friction and/or positive-locking connection such as, for example, by snap connection. Particularly preferably, the engagement element and/or the spacer sleeve of the cap is/are detachably connected to the needle protection sleeve. Moreover, the engagement element and/or the spacer sleeve may be connected in a rotationally fixed manner to the needle protection sleeve. Alternatively, the cap may be detachably connected to the housing, wherein the injection device may comprise one or no needle protection sleeve.

Additionally, reference is made to the features disclosed in connection with the device described herein, which also advantageously further comprise the device used for the method.

The device is described in reference to several figures. The features disclosed therein comprise variations of the invention, taken individually or in any combination of features. In the drawing:

FIG. 1a is an exploded view of an embodiment of an injection device according to the disclosure.

FIG. 1b is a perspective view of a rotating sleeve 3 of the injection device according to FIG. 1a.

FIG. 1c is a perspective view of a spacer sleeve 5 of the injection device according to FIG. 1a.

FIG. 3a is an exterior view of the injection device according to FIG. 2.

FIG. 3b is an exterior view of the injection device according to FIG. 3a, wherein a rotating sleeve 3 as seen in FIG. 3a is rotated about the longitudinal axis (L) by approximately 90°.

Figure 2:
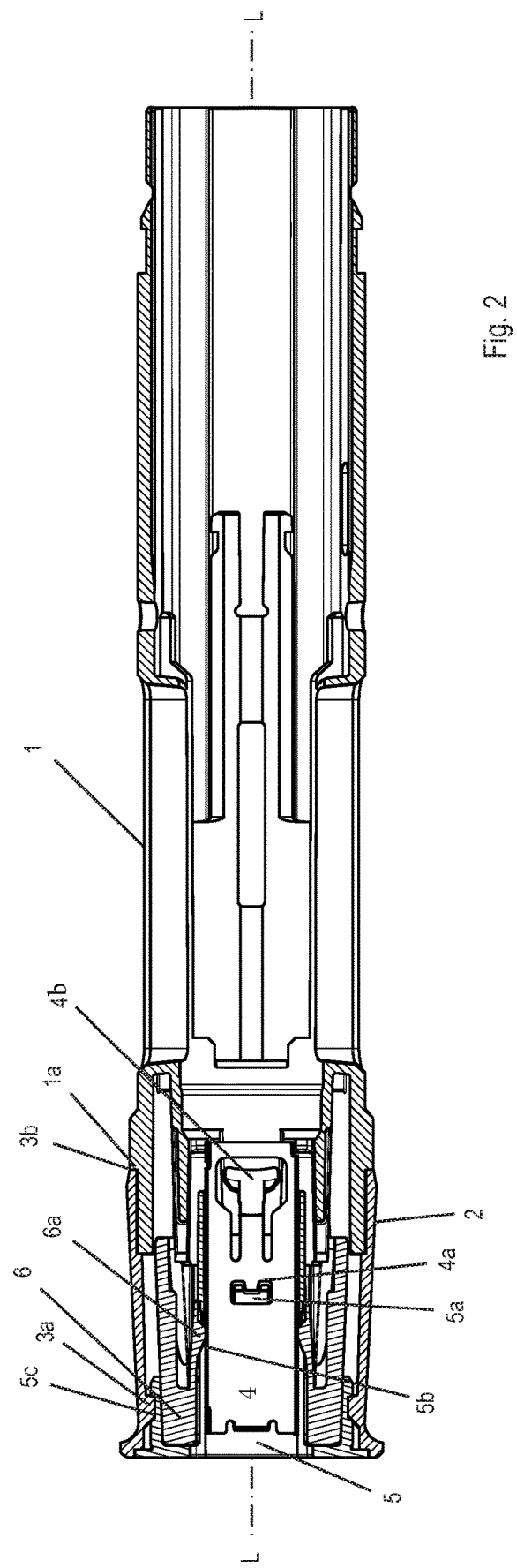
FIG. 2 is a longitudinal section of the injection device according to FIG. 1, wherein a cap 2 is detachably provided on a distal end of a housing 1 and wherein a product container with a needle protection cap is omitted for clarity.

In FIG. 1a, an exploded view of an embodiment of an injection device according to the invention can be seen. The injection device with a longitudinal axis L comprises a housing 1. The housing 1 can be formed as a sleeve-shaped, in particular a cylindrical receiving housing 1 with a distal and a proximal end. On the distal end of the housing 1, the cap 2 may be detachably provided. The housing 1 is used for receiving a product container (omitted for clarity), wherein the product container comprises a rigidly connected injection needle, wherein, on the product container, a needle protection cap is detachably arranged, which encloses the injection needle and seals it off in a sterile manner with respect to the environment. The injection device furthermore comprises a needle protection sleeve 6. The needle protection sleeve 6 can be shifted relative to the housing 1 of the injection device in the proximal direction for triggering product dispensing. The needle protection sleeve 6 is preferably connected in a rotationally fixed manner to the housing 1. After the product dispensing has occurred, the needle protection sleeve 6 can be shifted relative to the housing 1 in the distal direction, in order to cover the tip of the injection needle to reduce the risk of injury. The cap 2 comprises a rotating sleeve 3, one or more engagement elements 4 and a spacer sleeve 5. During the removal of the cap 2 from the injection device, the engagement element 4 is used to carry out the removal of the needle protection cap from the product container (omitted for clarity). For this purpose, the engagement element 4 is designed in the form of a hook 4b (see FIG. 2) or it comprises one or more hooks. The hook is designed in such a manner that the hook can engage in or on the needle protection cap, to be in an engagement position or reach an engagement position with the needle protection cap. The engagement element 4 is preferably made of metal, in particular steel, particularly preferably stainless steel or spring steel. The engagement element 4 is connected in an axially fixed and rotationally fixed manner to the spacer sleeve 5. For this purpose, the engagement element 4 has a recess 4a and the spacer sleeve 5 has a projection 5a (FIG. 2). The projection 5a of the spacer sleeve 5 is rigidly or detachably snapped into the recess 4a of the engagement element 4. The spacer sleeve 5 is designed in the shape of a sleeve or a cylinder. The spacer sleeve 5 is preferably made of plastic. Alternatively, the engagement element 4 and the spacer sleeve 5 may be designed to form a single piece and preferably be made of metal, in particular of steel, particularly preferably of stainless steel or spring steel. The cap 2 is preferably detachably connected via a snap-in connection between the spacer sleeve 5 and the needle protection sleeve 6 to the needle protection sleeve 6 and/or the housing 1. For this purpose, the needle protection sleeve 6 has a protrusion 6a (FIG. 2) which can detachably snap or protrude into a continuous or discontinuous opening 5b (FIG. 2) of the spacer sleeve 5. The cap 2 is thus provided detachably over the needle protection sleeve 6 on the distal end of the housing 1. In an alternative embodiment, the cap 2 can be detachably provided directly on the distal end of the housing 1. The rotating sleeve 3 at least partially receives the engagement element 4. Preferably, the rotating sleeve 3 and the engagement element 4 are arranged concentrically with respect to one another. The rotating sleeve 3 is arranged in such a manner that it can rotate relative to the housing 1 and relative to the engagement element 4 about the longitudinal axis (L). Particularly preferably, the rotating sleeve 3 and the spacer sleeve 5 may rotate in a guiding engagement in such a manner that the rotating sleeve 3 is rotatable relative to the spacer sleeve 5 about the longitudinal axis (L). For this purpose, the rotating sleeve 3 comprises a cam 3a on an inner lateral surface, which cam 3a is in engagement with an annular groove 5c of the spacer sleeve 5. The annular groove 5c is provided on an outer lateral surface of the spacer sleeve 5. The spacer sleeve 5 is connected in a rotationally fixed manner to the needle protection sleeve 6 and/or the housing 1. For this purpose, the spacer sleeve 5 comprises a longitudinal groove (5d) which is in engagement with a longitudinal web 10 (see FIG. 1a) of the needle protection sleeve 6. Alternatively, the spacer sleeve 5 can be connected in a rotationally fixed manner via a longitudinal web/longitudinal groove connection to the housing 1. Furthermore, the rotating sleeve 3 and the housing 1 each comprise a wave-shaped or curve-shaped guiding slide link (3b; 1a), which slide links are designed in such a manner and interact in such a manner that the rotating sleeve 3 can rotate relative to the housing 1 about the longitudinal axis (L) and the rotating sleeve 3 and the engagement element can move axially relative to the housing 1 in the distal direction. For this purpose, the rotating sleeve 3 comprises on a proximal end a wave-shaped or curve-shaped guiding slide link 3b and the housing 1 comprises on a distal end a corresponding wave-shaped or curve-shaped guiding slide link 1a. Particularly preferably, on an outer lateral surface of the housing 1, the housing 1 comprises a peripheral projection or web which forms the corresponding wave-shaped or curve-shaped guiding slide link 1a. The wave-shaped or curve-shaped guiding slide links of the rotating sleeve 3b and of the housing 1a are designed in such a manner and interact in such a manner (e.g., akin to cam action) that, after a relative rotation of the rotating sleeve 3 by approximately 90° about the longitudinal axis (L), the rotating sleeve 3 is moved into a distal position relative to the housing 1 (see FIG. 3b reflecting rotation relative to FIG. 3a). In the case of a relative rotation of the rotating sleeve by about 90° about the longitudinal axis (L), the rotating sleeve 3 is moved relative to the housing on an axial path in the distal direction, wherein, during the rotation of the rotating sleeve 3 about the longitudinal axis (L), an axial movement of the engagement element 4 in the distal direction occurs simultaneously.

Furthermore, the injection device comprises a reverse rotation lock mechanism, in particular in the form of a reverse rotation lock element and a reverse rotation lock counter-element, in order to enable a rotation of the rotating sleeve 3 about the longitudinal axis (L) in one direction and block it in the opposite direction. In an embodiment, the rotating sleeve 3 comprises a reverse rotation lock element and the spacer sleeve 5 comprises a reverse rotation lock counter-element in order to enable a rotation of the rotating sleeve 3 about the longitudinal axis (L) in one direction and block it in the opposite direction. The reverse rotation mechanism of the injection device is used to enable the user to rotate the rotating sleeve 3 in only one rotation direction about the longitudinal axis (L) relative to the engagement element 4 or relative to the housing 1. The rotating sleeve 3 can comprise a visual marking 7 (FIG. 1a), in particular in the form of a symbol, for example, an arrow, in order to indicate in which direction a rotation of the rotating sleeve 3 about the longitudinal axis (L) is possible.

In an embodiment, the rotating sleeve 3 can comprise a spring arm 8 (shown in phantom in FIG. 1b) which can be resiliently displaced, in particular resiliently displaced radially outward. The spring arm can preferably be arranged on an inner lateral surface of the rotating sleeve 3. The spacer sleeve 5 can comprise one or particularly preferably multiple grooves, in particular longitudinal grooves 9 (shown in phantom in FIG. 1b). The groove, particularly preferably the grooves, in particular the longitudinal grooves 9 are arranged distributed, in particular distributed regularly, on a lateral surface in circumferential direction. The spring arm 8 of the rotating sleeve 3 and the longitudinal grooves 9 of the spacer sleeve 5 are designed in such a manner and interact in such a manner that a rotation of the rotating sleeve 3 about the longitudinal axis (L) is possible in one direction and blocked in the opposite direction.

In another embodiment example, the rotating sleeve 3 can comprise a reverse rotation cam 3c, as represented in FIG. 1b. Particularly preferably, the rotating sleeve 3 comprises multiple reverse rotation cams 3c. Furthermore, the spacer sleeve 5 can comprise one or more reverse rotation projections 5e. The reverse rotation projection 5e of the spacer sleeve 5 can be formed in the shape of a tooth. The reverse rotation projection 5e of the spacer sleeve 5 is formed in the shape of a saw-tooth. The inclined surface of the reverse rotation projection 5e and the reverse rotation cam 3c of the rotating sleeve are designed in such a manner that the reverse rotation projection 5e, in the case of a rotation of the rotating sleeve 3 about the longitudinal axis (L), in particular in the case of a rotation of the rotating sleeve 3 about the longitudinal axis (L) in a first rotation direction, the reverse rotation cam 3c can slide over the inclined surface of the reverse rotation projection 5e. Furthermore, the steep surface of the reverse rotation projection 5e and the reverse rotation cam 3c of the rotating sleeve are designed in such a manner that the reverse rotation projection 5e blocks a rotation of the rotating sleeve 3 about the longitudinal axis (L), in particular a rotation of the rotating sleeve about the longitudinal axis (L) in a rotation direction opposite the first rotation direction.

In a particularly preferred embodiment example, as represented in FIG. 1c, the spacer sleeve 5 can comprise one or more pairs of reverse rotation projections 5e. A pair of reverse rotation projections 5e comprises two reverse rotation projections 5e which are arranged mutually offset with respect to one another in circumferential direction. This arrangement is used to enable the rotating sleeve 3 to rotate about the longitudinal axis (L) both in a first and/or in a second rotation direction, wherein, after the rotation in the first and/or in the second rotation direction, a rotation of the rotating sleeve 3 about the longitudinal axis (L) in a rotation direction opposite the first rotation direction and/or a rotation of the rotating sleeve 3 about the longitudinal axis (L) in a rotation direction opposite the second rotation direction is/are blocked.

In FIG. 2, a longitudinal section of the injection device according to FIG. 1 can be seen, wherein a cap 2 is detachably provided on the distal end of the housing 1 and wherein the product container with the needle protection cap is omitted for clarity and thus not seen. In FIG. 2, the injection device is represented in a delivery state, wherein the cap 2 is placed on the distal end. The cap 2 is detachably provided on the distal end of the housing 1, in particular via protrusion 6a of the needle protection sleeve 6 and via the opening 5b of the spacer sleeve 5 on the distal end of a needle protection sleeve 6. The rotating sleeve 3 can furthermore be detachably connected to the housing 1 of the injection device by a friction and/or positive-locking connection.

In FIG. 3a, an exterior view of the injection device according to FIG. 2 can be seen. FIG. 2 represents the injection device in the delivery state. The user rotates the rotating sleeve 3 in a direction, in particular in the direction shown on the rotating sleeve 3 in the form of a symbol, in particular in the form of an arrow 7, in order to detach the cap 2 from the injection device. Here, the detachable connection between the needle protection sleeve 6 and the spacer sleeve 5 is released, namely between the protrusion 6a of the needle protection sleeve 6 and the opening 5b of the spacer sleeve 5. Furthermore, during the rotation of the rotating sleeve 3 about the longitudinal axis (L), the friction and/or positive-locking connection between the rotating sleeve 3 and the housing 1 of the injection device can be released. In addition, the spring arm 8 of the rotating sleeve 3 slides over a groove 9, particularly preferably over the grooves, in particular over the longitudinal grooves, in order to enable a rotation of the rotating sleeve 3 in one direction and block it in the opposite direction. Alternatively, the reverse rotation cam 3c of the rotating sleeve 3 slides over the reverse rotation projection 5e of the spacer sleeve 5, in order to enable a rotation of the rotating sleeve 3 about the longitudinal axis (L) in one direction and block it in the opposite direction. Due to the axially fixed connection between the rotating sleeve 3 and the engagement element 4 and the wave-shaped or curve-shaped guiding slides (3b; 1b) between the rotating sleeve 3 and the housing 1, the engagement element 4 simultaneously moves in the distal direction. During a rotation of the rotating sleeve about the longitudinal axis (L) by approximately 90°, the rotating sleeve 3 and the engagement element 4 are moved relative to the housing on an axial path in distal direction, as represented in FIG. 3b. During the rotating and axial movement of the rotating sleeve 3 and during the axial movement of the engagement element 4 in the distal direction, the engagement element 4 reaches the engagement position or is in the engagement position with the needle protection cap, in order to carry out the removal of the needle protection cap from the product container. After the user has reached the distal position by rotating the rotating sleeve 3 about the longitudinal axis (L), the user can completely remove the cap 2 from the injection apparatus, in particular by an axial movement in distal direction, in order to actuate thereafter an injection by means of the injection device. In an alternative embodiment, the reverse rotation cam 3c of the rotating sleeve 3 slides over the reverse rotation projection 5e of the spacer sleeve 5 during the rotation of the rotating sleeve 3 about the longitudinal axis (L), when the rotating sleeve has reached the most distal position or shortly before the rotating sleeve has reached the most distal position.

LIST OF REFERENCE NUMERALS

1 Housing
1a Corresponding wave-shaped or curve-shaped guiding slide link
2 Cap
3 Rotating sleeve
3a Cam
3b Wave-shaped or curved-shaped guiding slide link
3c Reverse rotation cam
4 Engagement element
4a Recess
4b Hook
5 Spacer sleeve
5a Projection
5b Opening
5c Annular groove
5d Longitudinal groove
5e Reverse rotation projection
6 Needle protection sleeve
6a Protrusion
7 Marking for rotation direction (FIG. 1a)
8 Spring arm (FIG. 1b)
9 Groove (FIG. 1c)
10 Longitudinal web
L Longitudinal axis

The invention claimed is:

1. An injection device having a longitudinal axis with:
 a housing for receiving a product container with a rigidly connected injection needle, wherein, on the product container, a needle protection cap is detachably arranged, which encloses the injection needle and seals it in a sterile manner with respect to an environment;
 a cap which is detachably provided on a distal end of the housing;
 wherein the cap comprises an engagement element configured to carry out the removal of the cap from the injection device in order to carry out the removal of the needle protection cap from the product container;
 wherein the engagement element is arranged in a rotationally fixed manner relative to the housing;
 wherein the cap comprises a rotating sleeve which at least partially receives the engagement element and which can rotate relative to the housing and relative to the engagement element about the longitudinal axis, and which is arranged in an axially fixed manner relative to the engagement element,
 wherein the rotating sleeve and the housing each comprise a wave-shaped or curve-shaped guiding slide link, which slide links are configured to interact in such a manner that the rotating sleeve is rotatable relative to the housing about the longitudinal axis, and the rotating sleeve and the engagement element thereby move relative to the housing axially in the distal direction,
 wherein the rotating sleeve comprises a reverse rotation lock element and the engagement element or the housing comprises a reverse rotation lock counter-element in order to enable a rotation of the rotating sleeve in one direction and block it in the opposite direction.

2. The injection device according to claim 1, wherein the reverse rotation lock element of the rotating sleeve and/or the reverse rotation lock counter-element of the engagement element or of the housing comprise(s) a toothing or a latch or is/are formed as a toothing or a latch.

3. The injection device according to claim 1, wherein the reverse rotation lock element of the rotating sleeve and/or the reverse rotation lock counter-element of the engagement element or of the housing comprise(s) a spring arm or is formed as a spring arm.

4. The injection device according to claim 1, wherein the reverse rotation lock element of the rotating sleeve comprises one or more reverse rotation cams and the reverse rotation lock counter-element of the engagement sleeve or of the housing comprises one or more reverse rotation projections.

5. The injection device according to claim 4, wherein the one or more reverse rotation projections is in the shape of a saw-tooth.

6. The injection device according to claim 1, wherein the rotating sleeve, the engagement element and/or the housing comprise(s) a visual marking, to indicate in which direction a rotation of the rotating sleeve is possible.

7. The injection device according to claim 1, wherein the cap further comprises a spacer sleeve connected in an axially fixed and rotationally fixed manner to the engagement element and wherein the rotating sleeve is arranged to be rotatable relative to the spacer sleeve.

8. The injection device according to claim 7, wherein the rotating sleeve and the spacer sleeve are in a guiding engagement, such that the rotating sleeve is rotatable relative to the spacer sleeve about the longitudinal axis.

9. The injection device according to claim 1, wherein the engagement element comprises one or more hooks or is formed in the shape of a hook.

10. The injection device according claim 1, wherein the engagement element and the rotating sleeve are arranged concentrically with respect to one another.

11. The injection device according to claim 1, further comprising a needle protection sleeve, wherein the cap is detachably connected via the needle protection sleeve to the housing.

12. The injection device according to claim 1, wherein the wave-shaped or curve-shaped guiding slide link of the housing comprises or is formed as a projection or web which extends peripherally on or from an outer lateral surface of the housing.

13. A method for preparing an injection device for the administration of a product, having the following steps:
 providing an injection device according to claim 1,
 rotating the rotating sleeve about the longitudinal axis and simultaneously axially moving the engagement element in the distal direction, wherein the engagement element is or is brought into engagement with the needle protection cap.

14. The method of claim 13, wherein the step of providing an injection device according to claim 1, comprises providing an injection device and wherein the rotating sleeve, the engagement element and/or the housing comprise(s) a visual marking, to indicate in which direction a rotation of the rotating sleeve is possible.

15. The method of claim 13, wherein the step of rotating the rotating sleeve about the longitudinal axis and simultaneously axially moving the engagement element in the distal direction causes travel of the cap and performs removal of the cap from the injection device relative to the housing along the longitudinal axis (L) in the distal direction, which comprises a first partial travel during which the cap may be or is moved relative to the needle protection cap, and a second partial travel during which the needle protection cap also performs the movement of the cap or is entrained by the cap.

* * * * *